(12) United States Patent
Harris et al.

(10) Patent No.: US 6,193,692 B1
(45) Date of Patent: Feb. 27, 2001

(54) VERRES NEEDLE WITH HIGH FLOW ADAPTOR

(76) Inventors: Bruce C Harris, 1500 Carters Grove Rd., Clemmons, NC (US) 27012; Don E Mitchell, 4609 E. Fanfol Dr., Phoenix, AZ (US) 85028

( * ) Notice: Subject to any disclaimer, the term of this patent is extended or adjusted under 35 U.S.C. 154(b) by 0 days.

(21) Appl. No.: 09/128,552

(22) Filed: Aug. 3, 1998

(51) Int. Cl.[7] .................................................. A61M 5/178
(52) U.S. Cl. ....................... 604/164.02; 604/158; 604/26
(58) Field of Search ............................... 604/26, 30, 164, 604/93, 264, 158, 161, 246, 272, 502; 600/125

(56) References Cited

U.S. PATENT DOCUMENTS

| | | |
|---|---|---|
| 4,254,762 * | 3/1981 | Yoon ......................................... 128/4 |
| 4,601,710 | 7/1986 | Moll . |
| 4,808,168 | 2/1989 | Warring . |
| 4,869,717 * | 9/1989 | Adair ....................................... 604/51 |
| 4,902,280 | 2/1990 | Lander . |
| 5,098,388 | 3/1992 | Kulkashi et al. . |
| 5,104,381 | 4/1992 | Gresl et al. . |
| 5,421,821 | 6/1995 | Janicki et al. . |
| 5,478,329 | 12/1995 | Ternamian . |
| 5,685,852 * | 11/1997 | Turkel et al. ........................ 604/159 |

OTHER PUBLICATIONS

Skylar—Endoscopy Suction/Irrigation—Veress Needle.
Richard Wolf—Verres Needles VII.96 US.
Verres Needle, Reducer Blocker and Loop Guide, P. I–16, Printed Dec. 1995.
Hassan Open Laparoscopy, I–14, Printed Dec. 1995.
Aesculap—Supplemental Instruments, P. 1.

* cited by examiner

*Primary Examiner*—Richard K. Seidel
*Assistant Examiner*—Michael J. Hayes
(74) *Attorney, Agent, or Firm*—Robert W. Pitts

(57) ABSTRACT

A verres needle assembly includes an outer sheath member, a detachable stylet subassembly and a high flow adaptor that replaces the stylet subassembly. The outer sheath includes a cutting edge for making an initial surgical incision. The stylet subassembly is spring loaded to protect the cutting edge after the initial incision and also permit gas to be injected to partially inflate a body cavity. A simple half twist or luer lock connection allows the stylet subassembly to be easily removed and replaced by a high flow adaptor. Gas can then be injected through the outer sheath which remains in position after removal of the stylet subassembly without any internal restriction. The entire insufflation procedure takes less time than for a conventional verres needle.

15 Claims, 5 Drawing Sheets

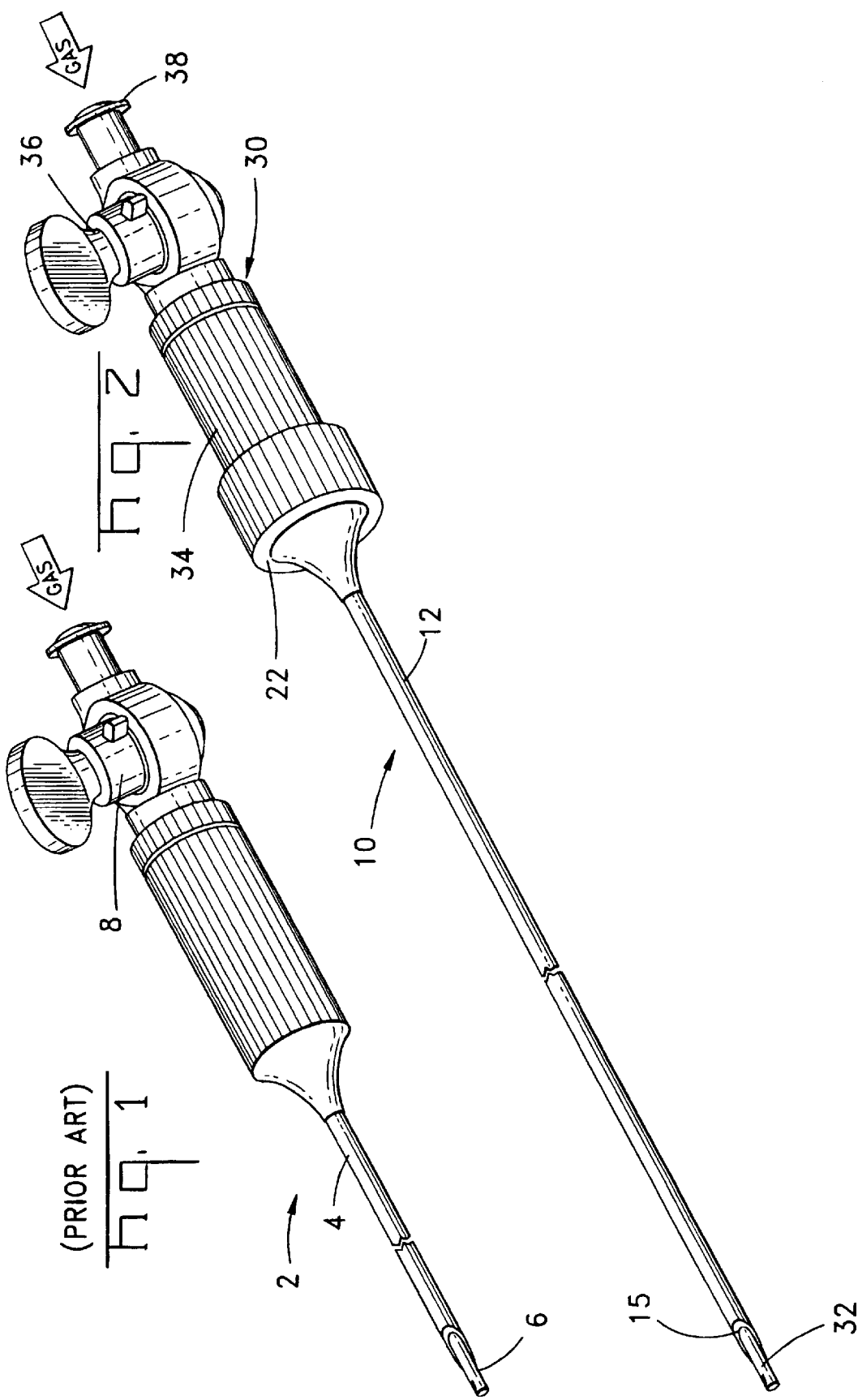

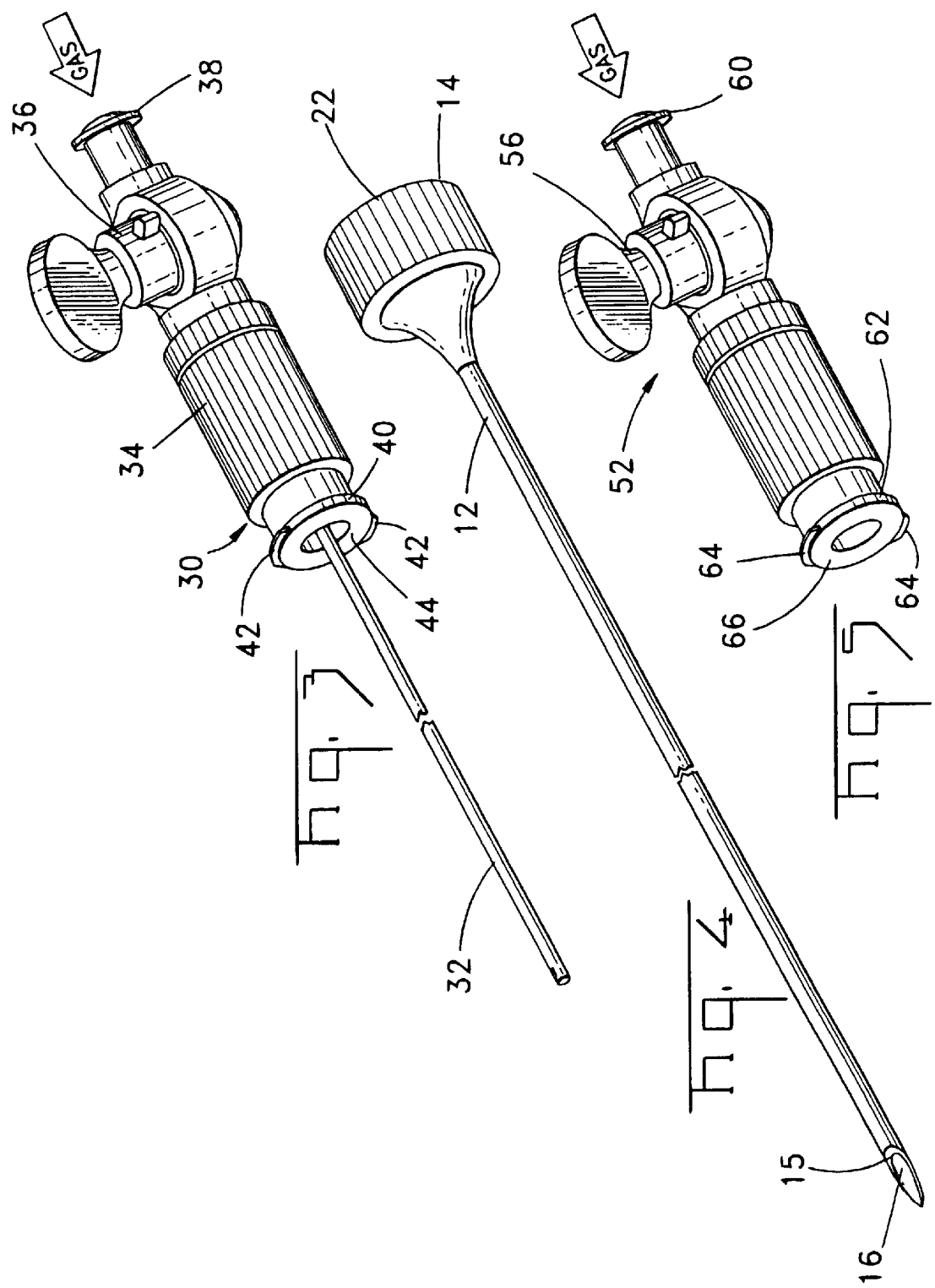

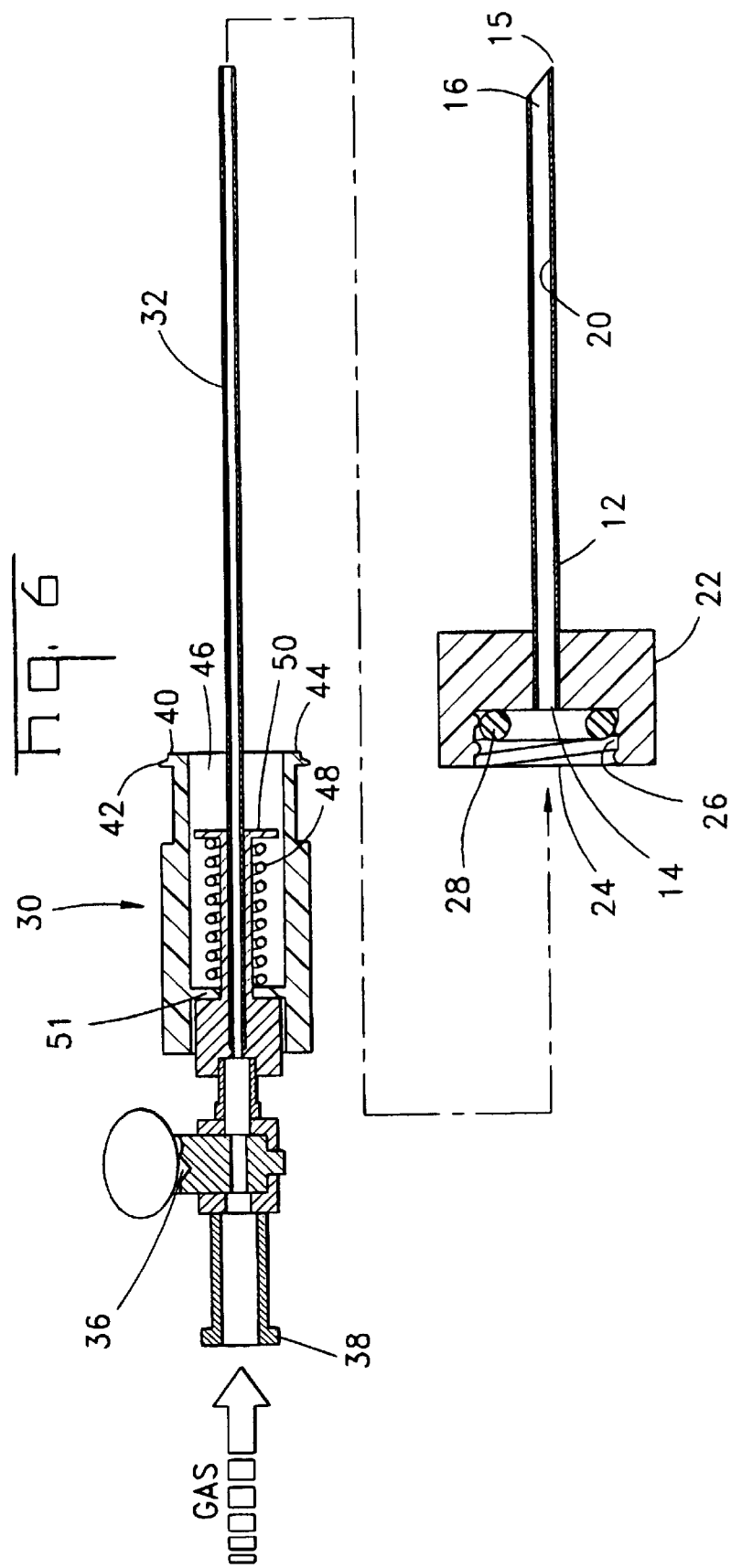

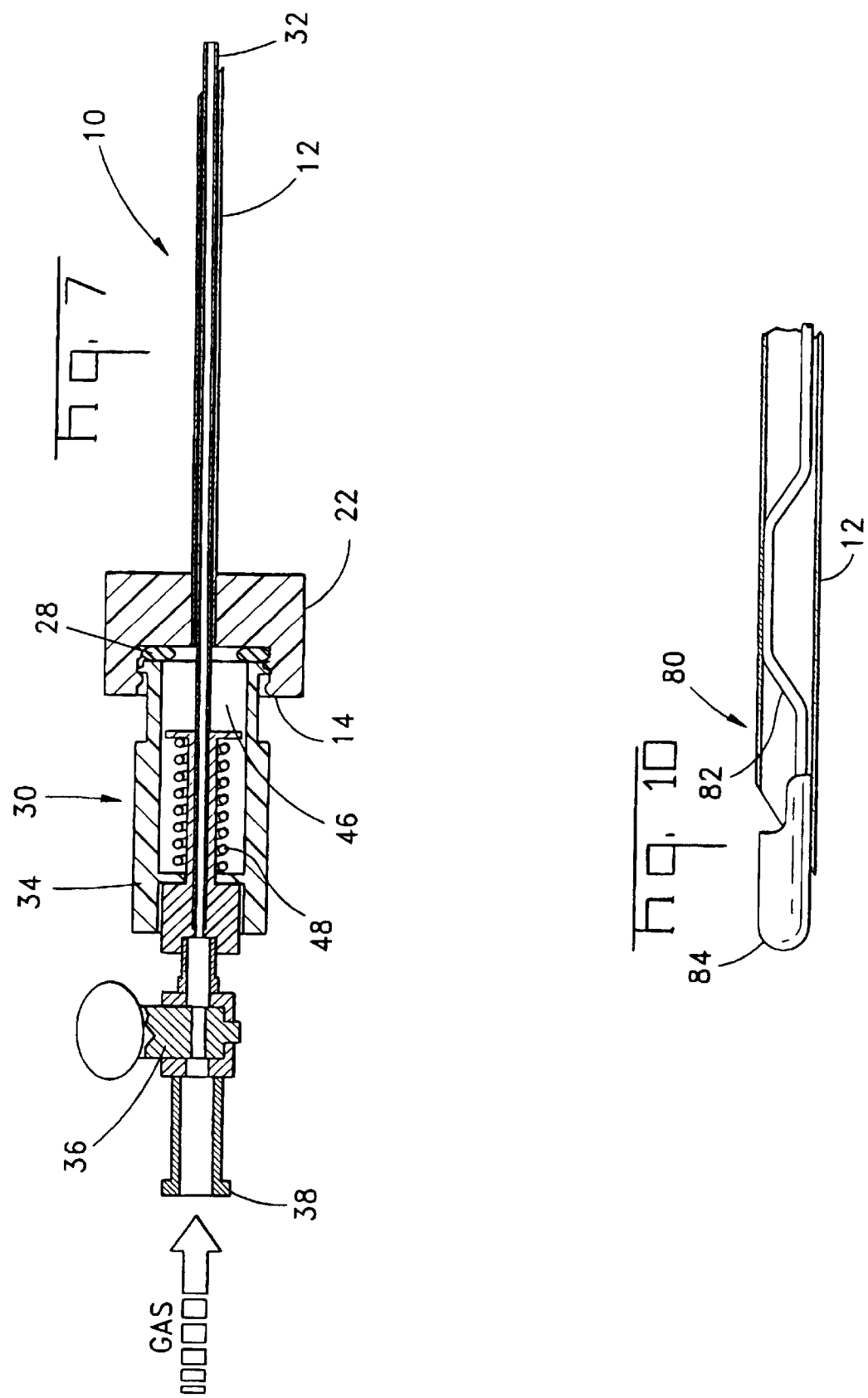

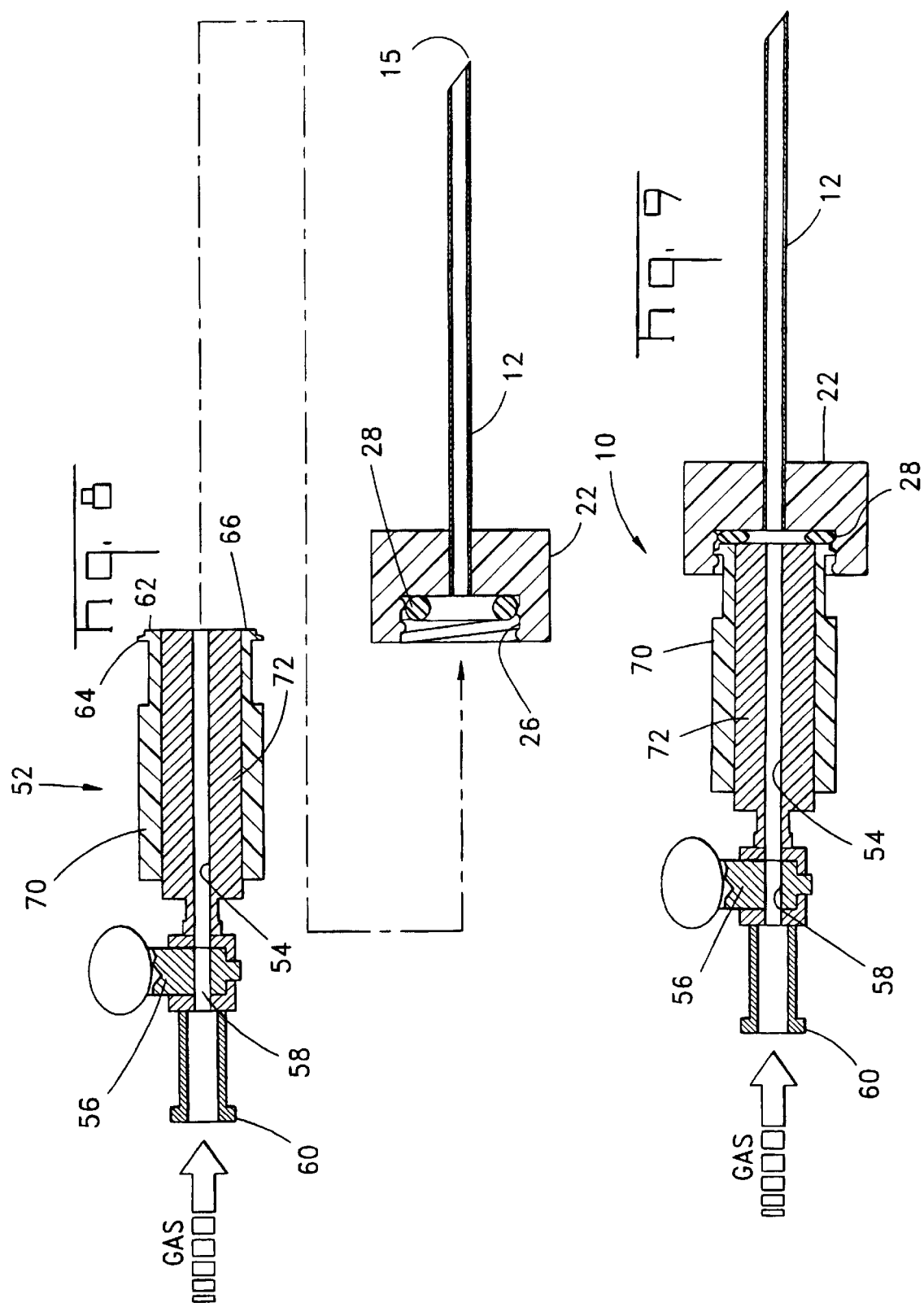

VERRES NEEDLE WITH HIGH FLOW ADAPTOR

BACKGROUND OF THE INVENTION

1. Field of the Invention

This invention is related to surgical instruments that are used in insuflation procedures. More particularly, this invention is related to the use of verres needles to inject a gas into a body cavity to facilitate endoscopic surgery.

2. Description of the Prior Art

Prior to performing an endoscopic procedure in a body cavity, such as the abdomen, it is necessary to insufflate the body cavity in order to separate the wall of the cavity from internal organs and to create space between the organs. This separation creates space within which a surgical procedure may be performed by the use of endoscopic instruments, such as laparoscopy instruments for abdominal surgery. The insufflation procedure typically involves insertion of a pneuomoneedle or verres pneumoneedle into the body cavity, after which a gas, such as carbon dioxide gas, at a pressure in excess of atmospheric is injected through the needle to inflate the body cavity. After the body cavity has been sufficiently inflated, the verres needle is removed and replaced by a larger diameter trocar to allow the introduction of surgical instruments without allowing gas to escape.

Prior art verres needles are typically used to create the initial incision in the body cavity wall. These prior art verres needles typically include a tubular outer sheath having an outer diameter of approximately 2.1 mm. This tubular sheath is fabricated of metal and the exposed or distal end of the tubular sheath includes a cutting edge of surface for effecting the initial incision. Since this cutting edge could cut or nick internal organs if it remained exposed, prior art verres needles typically include a spring loaded stylet having a relatively blunt leading end. This stylet includes an inner projection that extends through the tubular sheath with the blunt end located adjacent to the sharp cutting edge of the tubular sheath. A spring is located at the trailing end of the stylet and is located between the stylet and the body of the outer sheath. The spring normally urges the stylet beyond the exposed cutting edge of the outer sheath so that the cutting edge is not in a position to create an incision or to inadvertently cut or damage an internal organ or blood vessel when the style is in its extended position. However, when the blunt end of the stylet engages a surface, such as a body cavity wall that can exert a force on the stylet, the coil spring in the verres needle subassembly is compressed, retracting the stylet blunt end and exposing the cutting edge. After the cutting edge makes the initial incision in the body cavity wall, the force on the blunt end of the stylet is removed and the spring urges the stylet back into its extended position so that the cutting edge is again sheathed by the blunt end of the stylet.

After the initial incision is made by the verres needle, higher pressure gas is injected into the body cavity through the verres needle. The outer sheath of prior art verres needles are hollow and the leading end, which protrudes into the body cavity is open. Two types of stylets are used in conventional verres pneumoneedles. The inner projection of the first type is hollow and either is open on the blunt leading end or has a side opening passage adjacent the blunt leading end. In either case, air can pass through the inner bore of the stylet and out the exposed end of the verres needle into the body cavity. The other stylet consists of a solid inner projection having an outer diameter that is less than the inner diameter of the outer sheath. A gap between the periphery of the inner projection and the inner peripheral wall of the outer sheath permits the passage of gas through the outer sheath. This type verres needle normally has an enlarged tip that protrudes beyond the leading end of the outer sheath in the extended position. When the blunt tip is forced back into the sheath to expose the sheath cutting edge, the enlarged tip may close off the bore of the outer sheath. In the extended position, gas can escape between the open end of the outer sheath and the blunt stylet tip. In either type of conventional verres pneumoneedle, the cross sectional area within the outer sheath is significantly less than the inner diameter of the bore of the outer sheath. Therefore the mass flow rate of gas through the verres needle is restricted by this reduced cross sectional area. Since the time needed to insufflate a body cavity is proportional to the flow rate through the pneumoneedle, this restricted flow rate means that this procedure will take longer than for a higher flow rate. For conventional verres pneuoneedles, the the elapsed time for this procedure can be on the order of five (5) min. during which time the entire surgical staff must wait before performing other procedures. If this procedure required less time, the operation could be more efficiently performed because the surgical staff and the surgical facilities could be more efficiently employed. A reduction is the time needed to perform the entire operation could also reduce the stress on the patient.

SUMMARY OF THE INVENTION

These and other disadvantages of the prior art have been overcome by a verres needle assembly for use in an insufflating procedure, comprising an outer sheath, a detachable stylet subassembly and a high flow adaptor that replaces the stylet subassembly to permit an increased flow rate of gas into the body cavity. The outer sheath has an inner bore including a cutting edge for making an outer incision so that the outer sheath extends into a body cavity. The stylet subassembly includes an inner projection extending through the outer sheath. The inner projection is shiftable to protrude through a distal end of the outer sheath to allow air to be injected into the body cavity. The stylet subassembly is detachable from the outer sheath at a the mating ends of the outer sheath and the stylet subassembly. A high flow adapter can then be attached to the outer sheath at the mating end, after removal of the stylet subassembly. The adapter is attachable to a source of relatively higher pressure gas and has an internal bore larger than the open passage within the outer sheath and at least approximately the same size as the outer sheath inner bore. Gas can be injected into the body cavity through the outer sheath without flow restrictions between the proximal end of the adapter and the distal end of the outer sheath. A simple half twist or luer lock connection between the stylet subassembly and the outer sheath member and also between the high flow adaptor and the sheath member reduces the time required to replace the stylet subassembly with the high flow adaptor. This assembly reduces the time required to insufflate a body cavity as part of an endoscopic surgical procedure.

BRIEF DESCRIPTION OF THE DRAWINGS

FIG. 1 is a view of a prior art verres needle.

FIG. 2 is a view of a verres needle assembly including an outer sheath and a detachable stylet that is used for making an incision in a body cavity and for initially introducing a high pressure to insufflate the body cavity.

FIG. 3 is a view of a detachable stylet subassembly employed in the verres needle assembly shown in FIG. 2.

FIG. 4 is a view of the outer sheath member of the verres needle assembly of FIG. 2.

FIG. 5 is a view of a high flow adapter that can be attached to the outer sheath member of FIG. 4 to continue the insufflation procedure at a higher flow rate.

FIG. 6 is an exploded sectional view of the detachable stylet subassembly and the outer sheath member shown in FIG. 2.

FIG. 7 is a sectional view showing the detachable stylet subassembly attached to the outer sheath member.

FIG. 8 is an exploded sectional view showing the outer sheath member and the high flow adapter.

FIG. 9 is a sectional view showing the high flow adapter attached to the outer sheath member.

FIG. 10 shows an alternate embodiment of the stylet subassembly.

DETAILED DESCRIPTION OF THE PREFERRED EMBODIMENT

FIG. 1 is a view of a representative prior art verres pneumoneedle 2 which includes an outer sheath 4 and a spring loaded stylet 6. This verres needle also includes a valve 8 for regulating the flow of gas delivered from a relatively higher pressure source through a hose attached at the rear end of the needle. The outer sheath 4, the stylet 6 and the valve 8 and the spring biasing the stylet 6 relative to the sheath 4 are all parts of the same assembly. The stylet 6 is permanently mounted in a metal or molded housing from which the outer sheath extends. The tubular stylet projection is permanently encapsulated within the sheath 4 and the spring is located in the housing at the base of the tubular outer sheath 4. Some prior art verres needles of this type can either be intended for a single use while others can be used repeatedly.

The preferred embodiment of this invention shown in FIGS. 2–5 differs from the prior embodiment in that the verres needle assembly 10 comprises three subassemblies, an outer sheath member 12, a stylet subassembly 30 and high flow adaptor subassembly 52. Both the stylet subassembly 30 and the high flow adaptor subassembly 52 are detachable from the outer sheath member 12. The stylet subassembly 30 is attached to the outer sheath member 12 so that the initial incision into the body cavity and the initial injection of gas into the body cavity can be carried out in the same manner as with the prior art verres needle 2. However, after a small amount of gas has been injected into the body cavity to insure that no internal organs are in contact with the sharp cutting edge 15 on the distal end 16 of the outer sheath 12, the stylet subassembly 30 is removed from the outer sheath member 12. The high flow adaptor subassembly 52 is then attached to the outer sheath member 12 so that higher pressure gas can be injected into the body cavity at a higher rate. Therefore the entire insufflation procedure can be completed in less time.

The outer sheath member 12 comprises a tubular sheath that is joined to a cylindrical body 22 having an outer diameter that is greater than the diameter of the tubular sheath. The tubular sheath is substantially identical to the sheath 4 of the prior art verres needle and has the same inner diameter defined by the inner bore 20. Cutting edge 15 at the distal end 16 is shaped so that when exposed it will make an incision into the wall of the body cavity of the patient. The sheath body 22, located at the proximal end of the tubular sheath member 12 has internal threads or a spiral groove 26 formed along the internal diameter thereof. These threads or this groove are substantially identical to a female luer lock or half twist connection employed on syringes or catheters. An O-ring seal 28 fabricated from a conventional elastomeric material is mounted at the base of the threads 26. The outer sheath member 12 could be fabricated from a metal of the same type used for conventional verres needle with a hardness sufficient to form a cutting edge 15. The outer sheath member 12 could also be fabricated as a two piece member with a metal tube joined to a plastic body 22 by conventional means.

The stylet subassembly 30 includes a tubular inner projection 32 that extends through the tubular sheath 12 in the same manner as a for a conventional verres needle. This tubular projection 34 is joined to a cylindrical stylet housing 34 that, in conjunction with the sheath body 22 forms a surface that can be grasped by the surgeon to apply sufficient force to make the incision in the body cavity wall. A stylet valve 36 is located near the rear of the stylet housing 34 and a projecting hose coupling rib 38 is located to the rear of the valve 36 so that a hose connected to a source of gas, at a pressure greater than ambient or atmospheric, can be attached to the stylet subassembly 30.

The inner projection 32 on stylet subassembly 30 is a hollow tube with an opening adjacent the exposed end. This hollow tube 32 fits within the outer sheath 12. The inner diameter of the hollow tube or inner projection 32 is less than the inner diameter of the tubular outer sheath 12. Therefore, the flow rate through the hollow tube 32 is less than the rate of flow that could be achieved through the outer sheath 12 alone.

The inner projection 32 is spring biased or spring loaded relative to the stylet housing 34 and to the outer sheath member 12 to which the stylet subassembly is attached in the assembly configuration shown in FIG. 7. Spring 48 is located within the hollow outer portion of the cylindrical stylet housing 34. Spring 48 is trapped between a spring stop 50 and an inwardly projection flange 51 on the housing 34. This spring 48 normally urges or biases the inner projection 32 to its extended position shown in FIG. 7 in which the exposed end of the inner projection 32 extends beyond the distal sheath end 16 and more importantly beyond the cutting edge 15. In this position the cutting edge 15 cannot inadvertently damage an organ or membrane in the patient's body cavity. However, the strength of the spring 48 is chosen so that when the surgeon presses the tip of the verres needle 10 on a wall of the cavity, the inner projection 32 can retract exposing the cutting edge 15 to make an appropriate incision. After this incision is completed, there will no longer be a force action upon the tip of the inner projection 32, and the spring 48 will shift the inner projection 32 back to its extended or protective position.

The hollow tube 32 is aligned with an air passage extending from the rear of the stylet housing 34 though the valve or stop cock 36. The valve opening has a smaller internal diameter than the surrounding passage, but the size of the valve opening is approximately the same size as the inner bore 54 of the inner projection 32. The size of this inner bore 54 will therefore determine the gas flow rate though the verres pneumoneedle 10 at any given supply pressure.

The diameter of the mating end of the stylet housing 34 is dimensioned so that the stylet subassembly 30 can be attached to the sheath member 12. The mating end 46 can be inserted into the cylindrical opening at the mating end 24 of the sheath body 22. The mating end 46 includes a male luer lock configuration that is matable with the threads or grooves 26 on the sheath body 22. This luer lock configuration includes a radially projecting lip 40 with projecting ribs 42 located at opposite sides of the lip 20. A cylindrical projection or surface 44 at the end of the luer lock configuration is dimensioned to engage the O-ring seal 28 to prevent the gas from leaking at the interface between the stylet subassembly 30 and the sheath member 12. This configuration allows the male and female members to mate with a simple half twist or a rotation of approximately one hundred and eighty degrees of the stylet subassembly 30. More importantly for this invention the stylet subassembly 30 can be unmated or disengaged from the sheath member 12 by a simple half twist of the stylet subassembly 30. The entire stylet subassembly can then be extracted by pulling it away from the sheath member 12 and the patient. The sheath member 12 remains in place with the tubular sheath penetrating the body cavity which has been partially inflated before removal of the stylet subassembly 30.

The flow adaptor 52 is attached to the sheath member 12 after removal of the stylet subassembly 30. The flow adaptor 52 has an internal bore 54 extending between opposite ends that is at least approximately the same size as the inner bore 20 of the tubular sheath 12. The inner diameter of internal bore 54 is also greater than the internal diameter of the inner projection 32 of the stylet subassembly 30. The flow rate through flow adaptor 52 and outer sheath 12 will therefore be greater than the flow rate through the style subassembly for the same gas supply pressure. Adaptor 52 includes an inner sleeve 72 and an outer sleeve 70. The internal bore 74 extends between opposite ends of inner sleeve 72 and an adaptor valve or stop cock 56 is located adjacent to the rear of the adaptor 52. A hose coupling 60 is located at the rear end of adaptor 52. The outer sleeve 70 has a mating end 68 that has the same configuration as the mating end of the stylet subassembly 30. A luer lock projection 62 has two ribs 64 extending therefrom to engage the threads or grooves 26 on the sheath member 12. A cylindrical section 66 on the end of the luer lock configuration is dimensioned to engage and compress the O-ring seal 28 in the sheath body 22. The adaptor mating end 68 can therefore be attached to and disengaged from the sheath member 12 by a simple half twist motion in the same manner as the stylet subassembly 30.

After removal of the stylet subassembly 30 fro the outer sheath member 12, a surgeon can, if necessary place his finger over the open end of the sheath body 22 while the adaptor is prepared for mating to the sheath member 12. Although this removal and attachment operation does require some time, the use of a simple half twist sealed connection minimizes any lost time and the increased flow rate possible with the high flow adaptor results in a reduction of the time required to inssuflate a body cavity. To further reduce the time required to place the high flow adaptor 52 onto the outer sheath member 12, a simple Y connection to the hose leading from the gas supply can be incorporated so that it is not necessary to disconnect and reconnect the hose.

FIGS. 2–9 depict the preferred embodiment of this invention. However, numerous equivalent modifications apparent to one of ordinary skill in the art could be substituted. FIG. 10 shows one such modification. This stylet subassembly 80 includes a solid inner projection 82 with a plug section 84 at the end. This inner projection 82 is located within the tubular sheath 12 in the same manner as the inner projection 32. The flow path for this configuration is through the gap between the inner bore 20 and the solid projection 82. As with the preferred embodiment the cross sectional area of the flow path through the tubular sheath 12 is still restricted by this configuration. This stylet subassembly 80 is removable in the same manner as the stylet subassembly 30. In another equivalent modification, the valve could be part of a body including the tubular sheath. The portion containing the valve could be pivoted and the inner stylet projection and spring member could be removed from this outer body. These and other equivalent modifications can be made to the preferred embodiment can be made without departing from the invention as defined in the following claims.

We claim:

1. A verres needle assembly for use in an insufflating procedure, comprising:

an outer sheath having an inner bore including means on a distal end of the outer sheath for making an outer incision so that the outer sheath extends into a body cavity;

a stylet subassembly attachable to the outer sheath at a proximal end including an inner projection extending through the outer sheath, the inner projection being shiftable relative to the outer sheath to protrude through the distal end of the outer sheath to allow air to be injected into the body cavity though an open passage within the outer sheath, the stylet subassembly being detachable from the outer sheath at the proximal end of the outer sheath; and an adapter attachable to the outer sheath at the proximal end thereof, after removal of the stylet subassembly, the adapter being attachable to a source of gas, at a pressure higher than pressure in the body cavity, and having an internal bore larger than the open passage within the outer sheath when the stylet subassembly is attached to the outer sheath, and at least approximately the same size as the outer sheath inner bore so that gas can be injected into the body cavity through the outer sheath without flow restrictions between the proximal end of the adapter and the distal end of the outer sheath, the adaptor including a stop cock positionable with an opening in the stop cock in alignment with the inner bore of the outer sheath and the internal bore of the adapter to form a passage having a cross sectional area at least approximately the same as the cross sectional area of the outer sheath inner bore for the introduction of relatively higher pressure gas into a body cavity.

2. The verres needle assembly of claim 1 wherein the open passage within the outer sheath comprises an open inner bore of the stylet inner projection.

3. The verres needle assembly of claim 1 wherein the open passage within the outer sheath comprises a gap between the stylet inner projection and the inner bore of the outer sheath.

4. The verres needle assembly of claim 1 wherein the stylet subassembly includes a valve for regulating passage of a gas through the outer sheath when the stylet subassembly is attached to the outer sheath.

5. The verres needle assembly of claim 4 wherein the adapter includes a valve for regulating passage of a gas through the outer sheath when the adapter is attached to the outer sheath.

6. The verres needle assembly of claim 1 wherein the stylet subassembly and the adapter are attachable to the outer sheath by a luer lock connection.

7. The verres needle assembly of claim 6 wherein sealing means are located between the stylet subassembly and the outer sheath when attached and are located between the adapter and the outer sheath when attached.

8. The verres needle assembly of claim 7 wherein the sealing means comprises a O-ring seal located within the outer sheath.

9. The verres needle assembly of claim 6 wherein the luer lock connection comprises internal threads on the outer sheath and a protruding lip on the stylet subassembly and an outer rib on the adapter.

10. The verres needle assembly of claim 9 wherein stylet subassembly and the adapter include a cylindrical section extending beyond the outer lip thereon.

11. Apparatus for use in injecting a gas into a body cavity the gas having a pressure higher than pressure in the body cavity, comprising:

an outer sheath member including means for penetration into the body cavity, the outer sheath member including a tubular sheath with an inner bore and a body to which the tubular sheath is attached, the body including a first connection means on a mating end: and a flow member attachable to the outer sheath member, the flow member including means for attaching the flow member to a source of relatively higher pressure gas, a stop cock having an opening of at least approximately the same cross sectional area as the tubular sheath inner bore, a tubular section having an inner passage of at least approximately the same cross sectional area as the tubular sheath inner bore, and a second connection means, attachable to and detachable from the first connection means on the outer sheath member, located adjacent one end of the tubular section, wherein the stop cock is positionable with the opening in alignment with the tubular sheath and the tubular section of the flow member to form a passage having a cross sectional area at least approximately the same as the cross sectional area of the tubular sheath inner bore for the introduction of relatively higher pressure gas into a body cavity.

12. The apparatus of claim 11 wherein the first connection means comprises a female connector and the second connection means comprises a male connector.

13. The apparatus of claim 11 wherein a seal is located between the outer sheath body and the tubular section of the flow member.

14. The apparatus of claim 11 wherein the first and second connection means comprise half twist connection means.

15. The apparatus of claim 11 wherein the tubular sheath section comprises an inner tubular member and an outer tubular member, the second connection means being located on the exterior of the outer tubular member.

* * * * *